US006221066B1

(12) United States Patent
Ferrera et al.

(10) Patent No.: US 6,221,066 B1
(45) Date of Patent: Apr. 24, 2001

(54) SHAPE MEMORY SEGMENTED DETACHABLE COIL

(75) Inventors: David A. Ferrera, San Francisco; Daniel R. Kurz, Sunnyvale; Peter Wilson, Foster City, all of CA (US)

(73) Assignee: Micrus Corporation, Mountain View, CA (US)

( * ) Notice: Subject to any disclaimer, the term of this patent is extended or adjusted under 35 U.S.C. 154(b) by 0 days.

(21) Appl. No.: 09/264,927

(22) Filed: Mar. 9, 1999

(51) Int. Cl.$^7$ ..................................................... A61B 17/00
(52) U.S. Cl. ............................. 606/1; 606/108; 606/191; 623/11
(58) Field of Search ................................. 604/281, 104; 606/191, 198, 108, 1; 623/11, 1

(56) References Cited

U.S. PATENT DOCUMENTS

| | | |
|---|---|---|
| 1,341,052 | 5/1920 | Gale . |
| 1,667,730 | 5/1928 | Green . |
| 2,078,182 | 4/1937 | MacFarland . |
| 2,549,335 | 4/1951 | Rahthus . |
| 3,334,629 | 8/1967 | Cohn . |
| 3,649,224 | 3/1972 | Anderson et al. . |
| 3,868,956 | 3/1975 | Alfidi et al. . |
| 4,494,531 | 1/1985 | Gianturco . |
| 4,512,338 | 4/1985 | Balko et al. . |
| 4,638,803 | 1/1987 | Rand . |
| 4,655,771 | 4/1987 | Wallsten . |
| 4,718,907 | 1/1988 | Karwoski et al. . |
| 4,748,986 | 6/1988 | Morrison et al. . |
| 4,768,507 | 9/1988 | Fischell et al. . |
| 4,795,458 | 1/1989 | Regan . |
| 4,800,882 | 1/1989 | Gianturco . |
| 4,813,925 | 3/1989 | Anderson, Jr. et al. . |
| 4,820,298 | 4/1989 | Leveen et al. . |
| 4,830,003 | 5/1989 | Wolff et al. . |
| 4,850,960 | 7/1989 | Grayzel . |
| 4,856,516 | 8/1989 | Hillstead . |
| 4,954,126 | 9/1990 | Wallsten . |
| 4,955,862 | 9/1990 | Sepetka . |
| 4,957,479 | 9/1990 | Roemer . |
| 4,957,501 | 9/1990 | Lahille et al. . |
| 4,990,155 | 2/1991 | Wilkoff . |
| 4,994,069 | 2/1991 | Ritchart et al. . |

(List continued on next page.)

FOREIGN PATENT DOCUMENTS

| | | |
|---|---|---|
| 0 183 372 A1 | 6/1986 | (EP) . |
| 0 382014 A1 | 8/1990 | (EP) . |
| 2 066 839 | 7/1981 | (GB) . |
| WO 97/31672 | 4/1997 | (WO) . |

OTHER PUBLICATIONS

Christos A. Athanasoulis, M.D., The New England Journal of Medicine, May 15, 1980, "Therapeutic Applications of Angiography" pp. 1117–1125 (1 of 2).

(List continued on next page.)

*Primary Examiner*—Linda C. M. Dvorak
*Assistant Examiner*—Jocelyn Ram
(74) *Attorney, Agent, or Firm*—Fulwider Patton Lee & Utecht, LLP

(57) ABSTRACT

The shape memory segmented detachable coil assembly includes a plurality of hollow, tubular coil segments, and a plurality of connector members, with adjacent coil segments connected together by the connector members. The connector members are currently preferably hollow, tubular connector members that are advantageously detachable from selected portions of the coil segments by application of energy to one or more selected connector members. A heat activation member is used for heating one or more selected connector members to disconnect selected portions of the coil assembly. The heat activation member typically can be advanced axially through or over the coil assembly, and currently preferably comprises a fiber optic, although the heat activation member can also comprise a heat pipe, or a device for generating heat by RF energy or electrical resistance.

30 Claims, 1 Drawing Sheet

U.S. PATENT DOCUMENTS

| | | |
|---|---|---|
| 5,026,377 | 6/1991 | Burton et al. . |
| 5,041,084 | 8/1991 | DeVries et al. . |
| 5,064,435 | 11/1991 | Porter . |
| 5,071,407 | 12/1991 | Termin et al. . |
| 5,098,374 | 3/1992 | Othel-Jacobsen et al. . |
| 5,104,404 | 4/1992 | Wolff . |
| 5,108,407 | 4/1992 | Geremia et al. . |
| 5,122,136 | 6/1992 | Guglielmi et al. . |
| 5,129,890 | 7/1992 | Bates et al. . |
| 5,133,731 | 7/1992 | Butler et al. . |
| 5,133,732 | 7/1992 | Wiktor . |
| 5,141,502 | 8/1992 | Macaluso, Jr. . |
| 5,147,370 | 9/1992 | McNamara et al. . |
| 5,151,105 | 9/1992 | Kwan-Gett . |
| 5,160,341 | 11/1992 | Brenneman et al. . |
| 5,171,221 | 12/1992 | Samson . |
| 5,176,625 | 1/1993 | Brisson . |
| 5,176,661 | 1/1993 | Evard et al. . |
| 5,178,158 | 1/1993 | de Toledo . |
| 5,183,085 | 2/1993 | Timmermans . |
| 5,184,627 | 2/1993 | de Toledo . |
| 5,186,992 | 2/1993 | Kite, III . |
| 5,188,621 | 2/1993 | Samson . |
| 5,203,772 | 4/1993 | Hammerslag et al. . |
| 5,217,484 | 6/1993 | Marks . |
| 5,222,969 | 6/1993 | Gillis . |
| 5,226,911 | 7/1993 | Chee et al. . |
| 5,228,453 | 7/1993 | Sepetka . |
| 5,234,437 | 8/1993 | Sepetka . |
| 5,234,456 | 8/1993 | Silvestrini . |
| 5,250,071 | 10/1993 | Palermo . |
| 5,269,759 | 12/1993 | Hernandez et al. . |
| 5,304,194 | 4/1994 | Chee et al. . |
| 5,312,356 | 5/1994 | Engelson et al. . |
| 5,312,415 | 5/1994 | Palermo . |
| 5,336,205 | 8/1994 | Zenzen et al. . |
| 5,342,387 | 8/1994 | Summers . |
| 5,350,397 | 9/1994 | Palermo et al. . |
| 5,354,295 | 10/1994 | Guglielmi et al. . |
| 5,382,259 | 1/1995 | Phelps et al. . |
| 5,423,829 | 6/1995 | Pham et al. . |
| 5,441,516 | 8/1995 | Wang et al. . |
| 5,443,478 | 8/1995 | Purdy . |
| 5,514,176 * | 5/1996 | Bosley, Jr. ............................. 623/1 |
| 5,522,836 | 6/1996 | Palermo . |
| 5,540,680 | 7/1996 | Guglielmi et al. . |
| 5,542,938 | 8/1996 | Avellanet et al. . |
| 5,549,624 | 8/1996 | Mirigian et al. . |
| 5,562,641 | 10/1996 | Flomenblit et al. . |
| 5,569,245 | 10/1996 | Guglielmi et al. . |
| 5,582,619 | 12/1996 | Ken . |
| 5,607,445 | 3/1997 | Summers . |
| 5,624,449 | 4/1997 | Pham et al. . |
| 5,624,461 | 4/1997 | Mariant . |
| 5,637,113 | 6/1997 | Tartaglia et al. . |
| 5,639,277 | 6/1997 | Mariant et al. . |
| 5,643,254 | 7/1997 | Scheldrup et al. . |
| 5,649,949 | 7/1997 | Wallace et al. . |
| 5,667,522 | 9/1997 | Flomenblit et al. . |
| 5,676,697 | 10/1997 | McDonald . |
| 5,690,643 | 11/1997 | Wijay . |
| 5,690,666 | 11/1997 | Berenstein et al. . |
| 5,690,671 | 11/1997 | McGurk et al. . |
| 5,800,453 * | 9/1998 | Gia ....................................... 606/191 |
| 5,800,455 * | 9/1998 | Palermo et al. ..................... 606/191 |
| 5,814,062 | 9/1998 | Sepetka et al. . |
| 5,824,037 | 10/1998 | Fogerty et al. . |
| 6,022,369 * | 2/2000 | Jacobsen et al. .................... 606/191 |

OTHER PUBLICATIONS

Christos A. Athanasoulis, M.D., The New England Journal of Medicine, May 22, 1980, "Therapeutic Applications of Angiography" pp. 1174–1179 (2 of 2).

Alex Berenstein, M.D. and Irvin I. Kricheff, M.D., "Catheter and Material Selection for Transarterial Embolization: Technical Considerations" Radiology, Sep. 1979; pp. 631–639.

O.A. Battista, et al. Journal of Applied Polymer Science 1967 "Colloidal Macromolecular Phenomena. Part II. Novel Microcrystals of Polymers" pp. 481–498.

Sadek K. Hilal, M.D. et al. Journal of Neurological Surgery "Therapeutic Percutaneous Embolization for Extra–Axial Vascular Lesions of the Head, Neck and Spine" Sep., 1975; pp. 275–287.

Stephen L. Kaufman, M.D. et al. Investigative Radiology, May–Jun. 1978, "Transcatheter Embolization with Microfibrillar Collagen in Swine", pp. 200–204.

Ashok J. Kumar, et al., Journal of Neuroradiology (1982) "Preoperative Embolization of Hypervascular Head and Neck Neoplasms using Microfibrillar Collagen", pp. 163–168.

Richard E. Latchaw, M.D. et al., Radiology (1979) "Polyvinyl Foam Embolization of Vascular and Neoplastic Lesions of the Head, Neck and Spine" pp. 669–679.

Stewart R. Reuter, M.D. et al. American Journal of Radiology, Sep. 1975, "Selective Arterial Embolization for Control of Massive Upper Gastrointestinal Bleeding" pp. 119–126.

Glenn H. Roberson, et al., American Journal of Radiology, Oct. 1979, "Therapeutic Embolization of Juvenile Angiofibroma" pp. 657–663.

Sidney Wallace, M.D. et al., Cancer, Oct. 1979, "Arterial Occlusion of Pelvic Bone Tumors"; pp. 322–325 & 661–663.

"Mechanical Devices for Arterial Occlusion" by C. Gianturco, M.D., et al., Jul. 1975, pp. 428–435.

"Therapeutic Vascular Occlusion Utilizing Steel Coil Technique: Clinical Applications" by Sidney Wallace, et al., Am J. Roentgenol (1976); pp. 381–387.

"Transcatheter Intravascular Coil Occlusion of Experimental Arteriovenous Fistulas", by James H. Anderson, et al., Am. J. Roentgenol, Nov. 1977, pp. 795–798.

"'Mini' Gianturco Stainless Steel Coils for Transcatheter Vascular Occlusion" by James H. Anderson, et al., from The Department of Diagnostic Radiology at the University of Texas System Cancer Center, Aug. 1978, pp. 301–303.

"A New Improved Coil for Tapered–Tip Catheter for Arterial Occlusion" by Vincent P. Chuang, M.D., et al., May 1980, pp. 507–509.

* cited by examiner

SHAPE MEMORY SEGMENTED DETACHABLE COIL

BACKGROUND OF THE INVENTION

1. Field of the Invention

This invention relates generally to implantable devices for interventional therapeutic treatment or vascular surgery, and more particularly concerns an occlusion coil assembly with defined segments attached together by connector members that can be activated to release desired selected segments of the coil assembly.

2. Description of Related Art

Interventional vascular therapy and surgery has recently involved the use of catheters to place therapeutic devices at a treatment site by access through the vasculature. Examples of such procedures include transluminal angioplasty, placement of stents to reinforce the walls of a blood vessel or the like and the use of vasoocclusive devices to treat defects in the vasculature. One specific field of interventional therapy that has been able to advantageously use recent developments in technology is the treatment of neurovascular defects. One type of non-surgical therapy that has become advantageous for the treatment of defects in the neurovasculature has been the placement of vasoocclusive devices by way of a catheter in a damaged portion of a vein or artery.

Vasoocclusion devices are therapeutic devices that are placed within the vasculature of the human body, typically via a catheter, either to block the flow of blood through a vessel making up that portion of the vasculature through the formation of an embolus or to form such an embolus within an aneurysm stemming from the vessel. The vasoocclusive devices can take a variety of configurations, and are generally formed of one or more elements that are larger in the deployed configuration than when they are within the delivery catheter prior to placement. One widely used vasoocclusive device is a helical wire coil having a deployed configuration which may be dimensioned to engage the walls of the vessels. One anatomically shaped vasoocclusive device that forms itself into a shape of an anatomical cavity such as an aneurysm and is made of a pre-formed strand of flexible material that can be a nickel-titanium alloy is known from U.S. Pat. No. 5,645,558, which is specifically incorporated by reference herein. That vasoocclusive device comprises one or more vasoocclusive members wound to form a generally spherical or ovoid shape in a relaxed state. The device is sized and shaped to fit within a vascular cavity or vesicle, such as for treatment of an aneurysm or fistula. The vasoocclusive member can be first helically wound or braided in a generally linear fashion, and is then wound around an appropriately shaped mandrel or form, and heat treated to retain the shape after removal from the heating form. Radiopacity can be provided in the vasoocclusive members by weaving in synthetic or natural fibers filled with powdered radiopaque material, such as powdered tantalum, powdered tungsten, powdered bismuth oxide or powdered barium sulfate, which can potentially be released during vascular surgery.

The delivery of such vasoocclusive devices can be accomplished by a variety of means, including via a catheter in which the device is pushed through the catheter by a pusher to deploy the device. The vasoocclusive devices, which can have a primary shape of a coil of wire that is then formed into a more complex secondary shape, can be produced in such a way that they will pass through the lumen of a catheter in a linear shape and take on a complex shape as originally formed after being deployed into the area of interest, such as an aneurysm. A variety of detachment mechanisms to release the device from a pusher have been developed and are known in the art.

For treatment of areas of the small diameter vasculature such as a small artery or vein in the brain, for example, and for treatment of aneurysms and the like, micro-coils formed of very small diameter wire are used in order to restrict, reinforce, or to occlude such small diameter areas of the vasculature. A variety of materials have been suggested for use in such micro-coils, including nickel-titanium alloys, copper, stainless steel, platinum, tungsten, various plastics or the like, each of which offers certain benefits in various applications. Nickel-titanium alloys are particularly advantageous for the fabrication of such micro coils, in that they can have super-elastic or shape memory properties, and thus can be manufactured to easily fit into a linear portion of a catheter, but attain their originally formed, more complex shape when deployed.

In some applications, it has been found that the correct length of such microcoil occlusive devices for use at a treatment site in the vasculature is only determined after delivery of the device. Thus, typically a physician will choose a standard length, such as a 20 cm coil, for example, without knowing that only a 15 or 16 cm coil is the proper length. When it is discovered that a shorter coil is required, the entire coil needs to be removed and replaced with a shorter coil taking time to withdraw and replace with the proper length. In addition, if it is discovered that a longer coil is required, another procedure must be performed to supply the additional coil length. In either case, the entire treatment procedure is prolonged, resulting in potential trauma to the patient.

A need therefore remains for a microcoil occlusive device that will allow the precise required length of coil to be supplied to a desired treatment site in a minimally traumatic procedure. It would be desirable to provide a device that allows a physician to introduce a coil of ample length for any given treatment site in the vasculature, detach one or more desired coil lengths at the treatment site, and reposition the catheter and continue to deploy the remaining coil segments as desired, in a single procedure. The present invention meets these and other needs.

SUMMARY OF THE INVENTION

Briefly, and in general terms, the present invention provides for an occlusion coil assembly composed of detachable segments that can be detached and placed as desired at one or more vascular treatment sites, for use in interventional therapy and vascular surgery.

The invention accordingly provides for an occlusion coil assembly for use in interventional therapy and vascular surgery, adapted to be inserted into a portion of a vasculature of a patient. The occlusion coil assembly includes a plurality of hollow, tubular coil segments, and a plurality of connector members, with adjacent coil segments connected together by the connector members. The connector members are currently preferably hollow, tubular connector members that are advantageously detachable from selected portions of the coil segments by application of energy to one or more selected connector members. In a currently preferred embodiment, the connector members are formed of a shape memory material, preferably having a glass transition temperature ($T_g$) above body temperature, and having a desired stressed configuration at a temperature appropriate for introduction into the body via a catheter, and a more relaxed, unstressed original shape that is assumed upon activation for releasing the endoluminal therapeutic device. The shape memory material is currently preferably a shape memory polymer, such as polyurethane, heat shrink tubing such as polyethylene terephthalate (PET) or high density polyethylene (HDPE), although the shape memory material may alternatively be a shape memory metal such as nickel titanium alloy, such as that available under the trade name NITINOL, for example, that can be heat treated to have shape memory behavior.

The shape memory material sections are currently preferably secured to the coil segments by crimping a distal portion of a shape memory material connector member over a proximal portion of a segment of the coil assembly, and securing, such as by gluing, a proximal portion of the shape memory material connector member over a distal portion of a segment of the coil assembly. Alternatively, the shape memory material connector members can be secured to the coil segments such as by gluing a distal portion of a shape memory material connector member over a proximal portion of a coil segment, and crimping a proximal portion of the shape memory material connector member over a distal portion of a coil segment. As the sections are detached by heat activation, the activated shape memory material connector member radially opens and axially shrinks, separating one or more distal coil segments from the proximal portion of the coil assembly.

In operation of the occlusion coil assembly, a heat activation member is also preferably provided for heating one or more selected connector members to disconnect selected portions of the coil assembly. The heat activation member typically can be advanced and retracted axially through the middle of the coil assembly, or by means of a catheter that has a light source at the distal tip, for example, and currently preferably comprises a fiber optic, although the heat activation member can also comprise a heat pipe, or a device for generating heat by RF energy, or by electrical resistance, and the like.

From the above, it can be seen that the present invention provides an improved coil assembly that is more easily adapted to placement of coils without the risk of using an inappropriate length and the subsequent withdrawal and replacement of the coil by the therapist. These and other aspects and advantages of the invention will become apparent from the following detailed description and the accompanying drawings, which illustrate by way of example the features of the invention.

DETAILED DESCRIPTION OF THE PREFERRED EMBODIMENTS

Figure 1:
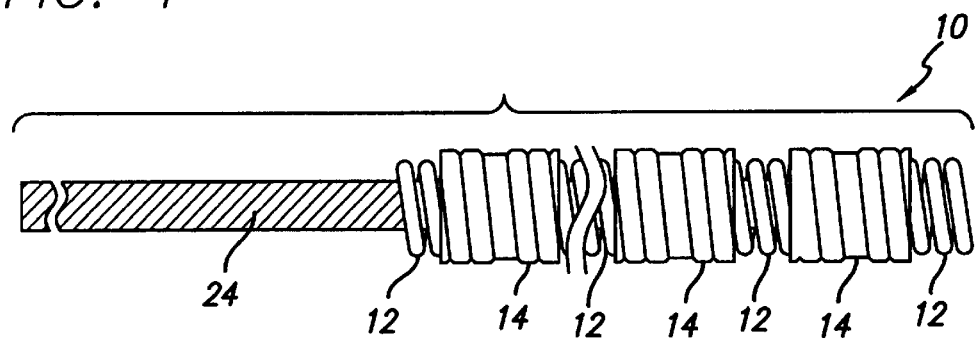
FIG. 1 is a side elevational view of the occlusion coil assembly of the present invention.
Figure 2:
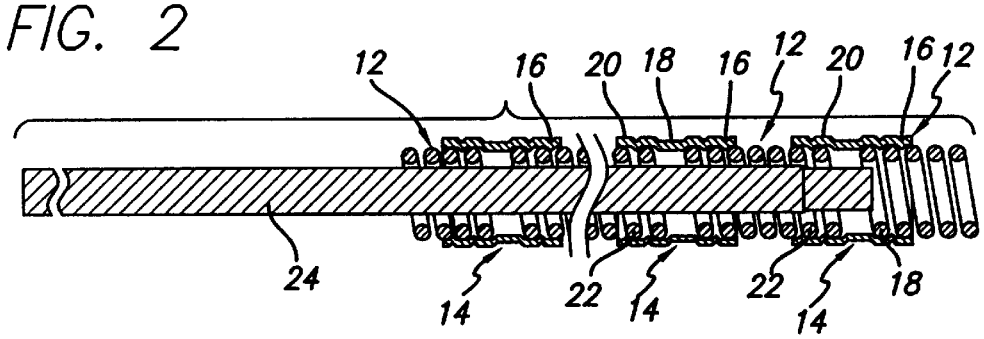
FIG. 2 is a cross-sectional view of the occlusion coil assembly of FIG. 1.
Figure 3:
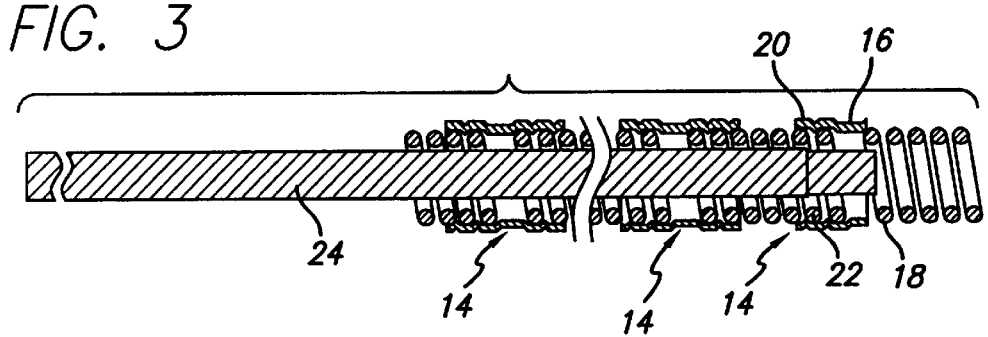
FIG. 3 is a cross-sectional view similar to FIG. 2, illustrating activation of a connector member and release of a segment of the occlusion coil assembly.

In the delivery of microcoil occlusive devices to a vascular treatment site, it is frequently necessary to remove and replace an incorrect length of the microcoil occlusive device with one of a desired length, requiring additional procedures and often causing further prolonged to a patient being treated.

As is illustrated in the drawings, the invention is accordingly embodied in an occlusion coil assembly 10 composed of a plurality of hollow, generally tubular coil segments 12 connected together by shape memory material connector members 14. The connector members are preferably formed of a shape memory material having a glass transition temperature ($T_g$) above body temperature, and having a desired stressed configuration at a temperature appropriate for introduction into the body via a catheter, and a more relaxed, unstressed original shape that is assumed upon activation for releasing the endoluminal therapeutic device. The shape memory material is currently preferably a shape memory polymer, such as polyurethane, heat shrink tubing such as polyethylene terephthalate (PET) or high density polyethylene (HDPE), although the shape memory material may alternatively be a shape memory metal such as nickel titanium alloy, such as that available under the trade name NITINOL, for example, that can be heat treated to have shape memory behavior.

The shape memory material connector members preferably have a stressed hollow, tubular configuration, and retract axially and expand radially when heated. Thus, in one currently preferred embodiment, the connector members can be secured in a stressed configuration to the coil segments by crimping a distal portion 16 of a shape memory material connector member over a proximal portion 18 of a distally adjacent segment of the coil assembly, and securing a proximal portion 20 of the shape memory material connector member over a distal portion 22 of a proximally adjacent segment of the coil assembly, such as by gluing with cyanoacrylate adhesive, for example. Alternatively, the shape memory material connector members can be secured in a stressed configuration to the coil segments, such as by gluing a distal portion of a shape memory material connector member over a proximal portion of a distally adjacent coil segment, with cyanoacrylate adhesive for example, and crimping a proximal portion of the shape memory material connector member over a distal portion of a proximally adjacent coil segment. When aligned and connected end to end, the coil assembly can typically form a coil about 30 cm long, while individual segments can typically be about 2 cm long.

The shape memory material connector members preferably can be caused to disconnect selected portions of the coil assembly by activation with a heat activation member 24, such as a fiber optic, that can be threaded through the coil segments although other heat transmission members such as a heat pipe, or a device generating heat by RF energy, or by electrical resistance, for example, may also be suitable. As the sections are detached by heat activation, the activated shape memory material connector member radially opens and axially shrinks, separating one or more distal coil segments from the proximal portion of the coil assembly.

Figure 4:
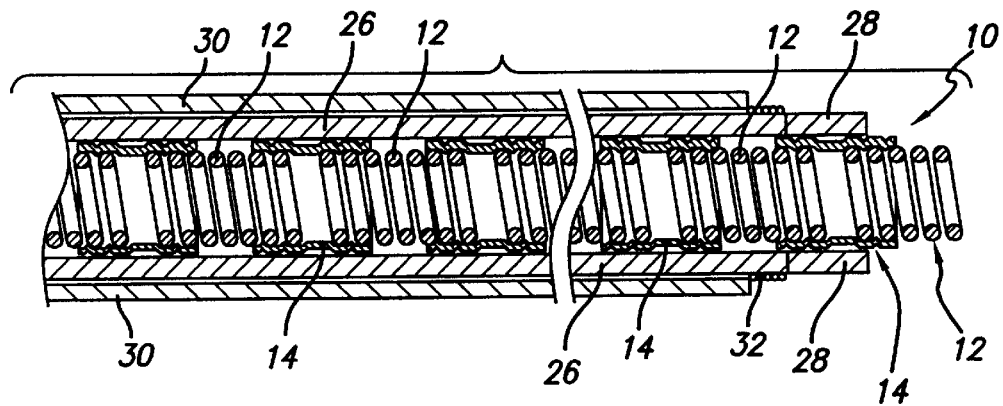
FIG. 4 is a cross-sectional view of an alternative embodiment of a heat activation member for release of a segment of the occlusion coil assembly.

In an alternative embodiment illustrated in FIG. 4, a heat activation member can also be threaded over the outside of the occlusion coil segments and connector members, such as a fiber optic tube 26 with an etched heat dissipation ring portion 28 that can be advanced and retracted within a catheter 30 along a coil assembly, and positioned around a desired connector member for heating and activating the connector member to release one or more coil segments, as described above. The heat activation member may advantageously be provided with a radiopaque section 32, such as a platinum, gold, or tungsten coil, for example, to allow the heat activation member to be imaged; and the coil segments may also be provided with similar radiopaque material to allow the coil segments to be imaged during placement at a vascular treatment site.

It will be apparent from the foregoing that while particular forms of the invention have been illustrated and described, various modifications can be made without departing from the spirit and scope of the invention. Accordingly, it is not intended that the invention be limited, except as by the appended claims.

What is claimed is:

1. An occlusion coil assembly for use in interventional therapy and vascular surgery, comprising:
    a plurality of hollow, tubular coil segments; and
    at least one hollow, tubular connector member, adjacent ones of said coil segments being connected together by said connector member, said connector member being detachable from selected portions of said coil segments by application of energy to said connector member.

2. The occlusion coil assembly of claim 1, further comprising a plurality of connector members.

3. The occlusion coil assembly of claim 1, wherein said connector member is formed from a shape memory material.

4. The occlusion coil assembly of claim 3, wherein said shape memory material has a desired stressed configuration at a temperature appropriate for introduction into the body via a catheter, and after placement, will take on a more relaxed, unstressed original shape for releasing the endoluminal therapeutic device.

5. The occlusion coil assembly of claim 3, wherein said shape memory material comprises a shape memory polymer selected from the group consisting of polyurethane, heat shrink tubing, polyethylene terephthalate, and high density polyethylene.

6. The occlusion coil assembly of claim 3, wherein said shape memory material is a nickel titanium alloy.

7. The occlusion coil assembly of claim 1, wherein said connector member is secured to adjacent coil segments by crimping a distal portion of one of said connector members over a corresponding proximal portion of a distally adjacent coil segment, and gluing a proximal portion of said connector member over a distal portion of a corresponding proximally adjacent coil segment.

8. The occlusion coil assembly of claim 1, wherein said connector member is secured to adjacent coil segments by crimping a proximal portion of one of said connector member over a corresponding distal portion of a proximally adjacent coil segment, and gluing a distal portion of said connector member over a proximal portion of a corresponding distally adjacent coil segment.

9. The occlusion coil assembly of claim 1, further comprising a heat activation member that can be advanced and retracted axially through said coil segments and said connector members for heating selected ones of said connector members to disconnect selected coil segments.

10. The occlusion coil assembly of claim 9, wherein said heat activation member comprises a fiber optic.

11. The occlusion coil assembly of claim 9, wherein said heat activation member comprises a heat pipe.

12. The occlusion coil assembly of claim 9, wherein said heat activation member comprises a device for generating heat by RF energy.

13. The occlusion coil assembly of claim 9, wherein said heat activation member comprises a device for generating heat by electrical resistance heating.

14. The occlusion coil assembly of claim 1, further comprising a heat activation member that can be advanced and retracted axially over said coil segments and said connector members for heating selected ones of said connector members to disconnect selected coil segments.

15. The occlusion coil assembly of claim 14, wherein said heat activation member comprises a fiber optic.

16. The occlusion coil assembly of claim 14, wherein said heat activation member comprises a device for generating heat by RF energy.

17. The occlusion coil assembly of claim 14, wherein said heat activation member comprises a device for generating heat by electrical resistance heating.

18. An occlusion coil assembly for use in interventional therapy and vascular surgery, comprising:
    a plurality of hollow, tubular coil segments;
    a plurality of connector members, adjacent ones of said coil segments being connected together by one of said connector members, said connector members being detachable from selected portions of said coil segments by application of energy to selected ones of said connector members; and
    a heat activation member that can be advanced and retracted axially adjacent to said coil segments and said connector members for heating selected ones of said connector members to disconnect selected coil segments.

19. The occlusion coil assembly of claim 18, wherein said connector members are formed from a shape memory material.

20. The occlusion coil assembly of claim 19, wherein said connector members have a hollow, tubular configuration.

21. The occlusion coil assembly of claim 19, wherein said shape memory material has a desired stressed configuration at a temperature appropriate for introduction into the body via a catheter, and after placement, will take on a more relaxed, unstressed original shape for releasing the endoluminal therapeutic device.

22. The occlusion coil assembly of claim 19, wherein said shape memory material comprises a shape memory polymer selected from the group consisting of polyurethane, heat shrink tubing, polyethylene terephthalate, and high density polyethylene.

23. The occlusion coil assembly of claim 19, wherein said shape memory material is a nickel titanium alloy.

24. The occlusion coil assembly of claim 18, wherein said connector members are secured to adjacent coil segments by crimping a distal portion of one of said connector members over a corresponding proximal portion of a distally adjacent coil segment, and gluing a proximal portion of said connector member over a distal portion of a corresponding proximally adjacent coil segment.

25. The occlusion coil assembly of claim 18, wherein said connector members are secured to adjacent coil segments by crimping a proximal portion of one of said connector members over a corresponding distal portion of a proximally adjacent coil segment, and gluing a distal portion of said connector member over a proximal portion of a corresponding distally adjacent coil segment.

26. The occlusion coil assembly of claim 18, wherein said heat activation member comprises a fiber optic.

27. The occlusion coil assembly of claim 18, wherein said heat activation member comprises a heat pipe.

28. The occlusion coil assembly of claim 18, wherein said heat activation member comprises a device for generating heat by RF energy.

29. The occlusion coil assembly of claim 18, wherein said heat activation member comprises a fiber optic tube having an etched heat dissipation ring portion.

30. The occlusion coil assembly of claim 18, wherein said heat activation member comprises a device for generating heat by electrical resistance heating.

* * * * *

UNITED STATES PATENT AND TRADEMARK OFFICE
CERTIFICATE OF CORRECTION

PATENT NO. : 6,221,066 B1
DATED : April 24, 2001
INVENTOR(S) : David A. Ferrera, Daniel R. Kurz, Peter Wilson It is certified that error appears in the above-identified patent and that said Letters Patent is hereby corrected as shown below:

Tiltle page,
Page 2, under "U.S. PATENT DOCUMENTS", add:
-- 5,853,418    12/1998    Ken et al. --.

Under "FOREIGN PATENT DOCUMENTS", add:
-- 96/00034      1/1996  (WO)
   0 829 236 A1  3/1998  (EP)
   0 948 935 A1  10/1999 (EP)
   99/42038      8/1999  (WO) --.

Under OTHER DOCUMENTS, add the following:
-- "International Search report, published Jul. 5, 2000 --.

Signed and Sealed this

Eleventh Day of September, 2001

Attest:

NICHOLAS P. GODICI
*Attesting Officer*    *Acting Director of the United States Patent and Trademark Office*